United States Patent [19]

House

[11] 4,287,988

[45] Sep. 8, 1981

[54] SYRINGE SHEATH GUIDE

[75] Inventor: Richard F. House, St. Charles, Ill.

[73] Assignee: Container Corporation of America, Chicago, Ill.

[21] Appl. No.: 130,573

[22] Filed: Mar. 14, 1980

[51] Int. Cl.³ ............................................. B65D 85/24
[52] U.S. Cl. ..................................... 206/365; 128/253
[58] Field of Search ............... 206/365, 367, 364, 380, 206/210; 128/253

[56] References Cited

U.S. PATENT DOCUMENTS

| | | | |
|---|---|---|---|
| 1,518,531 | 12/1924 | Linig | 206/365 |
| 2,110,123 | 3/1938 | Eisele | 206/365 |
| 3,055,364 | 9/1962 | Myerson | 206/365 |
| 3,112,031 | 11/1963 | Stewart | 206/364 |
| 3,648,704 | 3/1972 | Jackson | 206/364 |
| 4,214,659 | 7/1980 | Jaeschke | 206/365 |

FOREIGN PATENT DOCUMENTS

| | | | |
|---|---|---|---|
| 215604 | 11/1960 | Austria | 206/364 |
| 366105 | 12/1922 | Fed. Rep. of Germany | 206/364 |
| 696893 | 10/1940 | Fed. Rep. of Germany | 206/364 |

Primary Examiner—Herbert F. Ross
Attorney, Agent, or Firm—R. W. Carpenter; Davis Chin

[57] ABSTRACT

A one-piece, molded plastic device for protecting and guiding the needle sheath of a hypodermic syringe into the cavity of a package.

2 Claims, 7 Drawing Figures

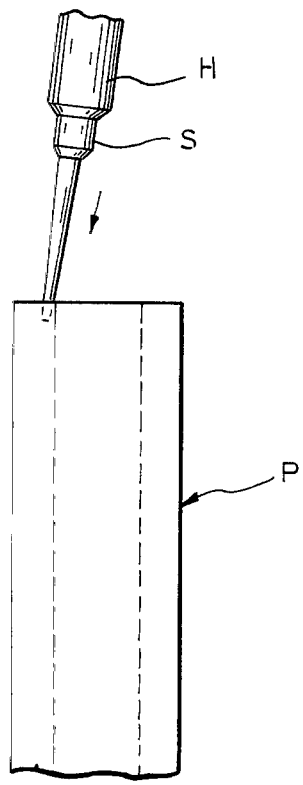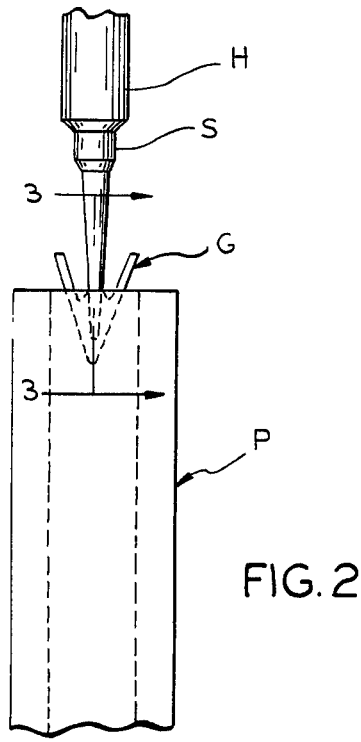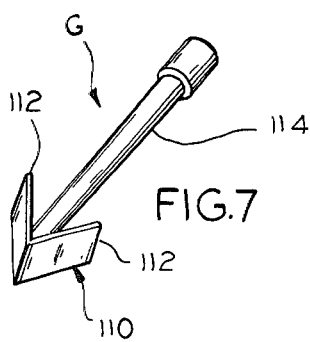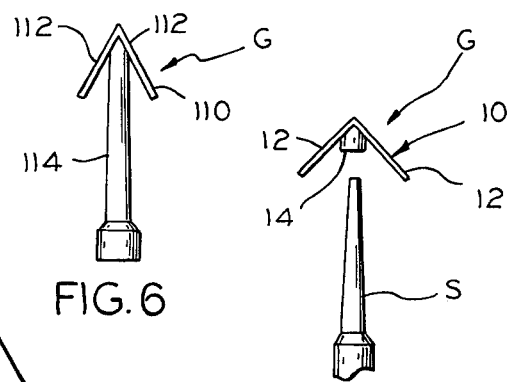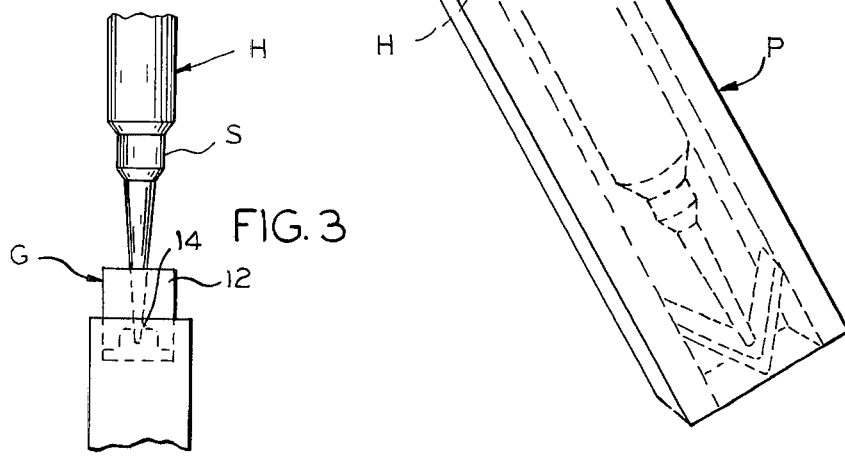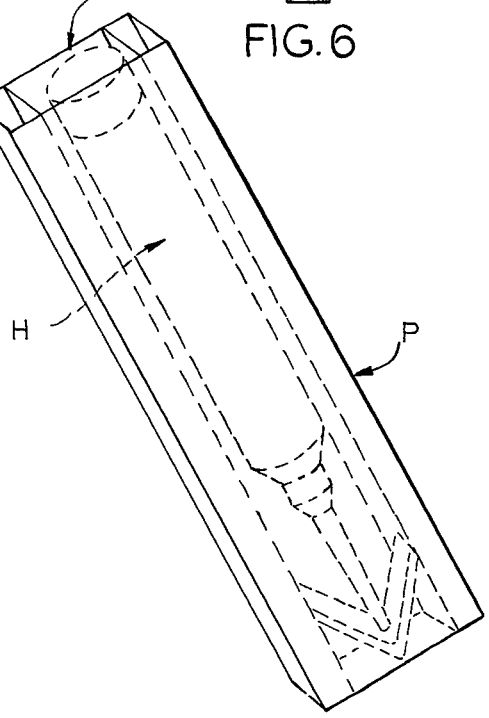

SYRINGE SHEATH GUIDE

SUMMARY OF THE INVENTION

This invention relates to a plastic device for assisting in and expediting the packaging of hypodermic syringes.

It is an object of the invention to provide a device for receiving and guiding the needle sheath of a hypodermic syringe into the cavity of a package.

A more specific object of the invention is the provision of a one-piece, wedge shaped guide device for hypodermic syringes.

These and other objects of the invention will be apparent from an examination of the following description and drawings.

THE DRAWINGS

FIG. 1 is a perspective view of a hypodermic syringe shown positioned within a cavity of a package;

FIG. 2 is a side elevation illustrating the insertion of a hypodermic syringe into a package by means of a guide device embodying features of the invention;

FIG. 3 is a side view in partial section taken on line 3—3 of FIG. 2;

FIG. 4 is a view similar to FIG. 2 but illustrating the manner in which a hypodermic syringe can be improperly inserted into a package without the benefit of the guide device embodying the invention;

FIG. 5 is a side view of a guide device embodying features of the invention;

FIG. 6 is a view similar to FIG. 5 but illustrating a modified form of the invention; and FIG. 7 is a perspective view of the structure illustrated in FIG. 6.

It will be understood that, for purposes of clarity, certain elements may have been intentionally omitted from certain views where they are believed to be illustrated to better advantage in other views.

DESCRIPTION OF THE INVENTION

Referring now to the drawings for a better understanding of the invention, it will be seen that shown within the cavity C of a conventional package P is a hypodermic syringe H having a removable sheath S for protection of the needle and having attached to the sheath a guide device G embodying features of the invention. As best seen in FIG. 5, guide G is a one-piece molded plastic structure which includes a plow or wedge 10 formed from a pair of relatively thin, flat blades 12 which are joined at their forward edges and which diverge rearwardly from each other.

Formed integrally with wedge 10 at the juncture of blades 12 is a rearwardly extending cylindrical collar or sleeve 14 which is adapted to receive the forward portion of the sheath of a hypodermic syringe to assist in guiding it into the cavity C of a package P as best shown in FIG. 2.

FIGS. 6 and 7 show a modified form of the invention wherein the wedge 110 is formed by a pair of blades 112, in the same manner as the structure of FIG. 5, but wherein the collar or sleeve 114 is elongated and has the same shape as a syringe sheath so that it can be used to either enclose the entire sheath or the hypodermic needle itself without requiring a sheath.

I claim:

1. A one-piece molded plastic device for protecting and guiding the needle sheath portion of a hypodermic syringe into the cavity of a package, comprising:
    (a) a pair of relatively thin, flat blades, joined at their forward edges and diverging rearwardly to form a wedge shaped structure;
    (b) a hollow cylindrical sleeve formed integrally with the blades of said wedge shaped structure and extending rearwardly therefrom for removably receiving a forward portion of a syringe sheath.

2. A one-piece molded plastic device for protecting and guiding the needle portion of a hypodermic syringe into the cavity of a package, comprising:
    (a) a pair of relatively thin, flat blades, joined at their forward edges and diverging rearwardly to form a wedge shaped structure;
    (b) a hollow cylindrical sleeve formed integrally with the blades of said wedge shaped structure and extending rearwardly therefrom for removably receiving the needle portion of a syringe.

* * * * *